(12) United States Patent
Hassett

(10) Patent No.: US 8,557,300 B2
(45) Date of Patent: Oct. 15, 2013

(54) METHODS FOR TREATING BACTERIAL RESPIRATORY TRACT INFECTIONS IN AN INDIVIDUAL USING ACIDIFIED NITRITE

(75) Inventor: Daniel J. Hassett, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 875 days.

(21) Appl. No.: 11/912,302

(22) PCT Filed: May 18, 2006

(86) PCT No.: PCT/US2006/019336
§ 371 (c)(1),
(2), (4) Date: Jun. 13, 2008

(87) PCT Pub. No.: WO2006/125123
PCT Pub. Date: Nov. 23, 2006

(65) Prior Publication Data
US 2008/0260865 A1    Oct. 23, 2008

Related U.S. Application Data

(60) Provisional application No. 60/682,577, filed on May 19, 2005.

(51) Int. Cl.
*A61K 9/12* (2006.01)
*A61K 33/00* (2006.01)

(52) U.S. Cl.
USPC ............................. 424/718; 424/45; 424/600

(58) Field of Classification Search
None
See application file for complete search history.

(56) References Cited

U.S. PATENT DOCUMENTS

| | | |
|---|---|---|
| 3,865,942 A | 2/1975 | Wirth |
| 4,163,790 A | 8/1979 | Franko et al. |
| 4,211,782 A | 7/1980 | Vane et al. |
| 4,849,226 A | 7/1989 | Gale |
| 5,263,473 A | 11/1993 | McWhorter |
| 5,366,997 A | 11/1994 | Keefer et al. |
| 5,389,675 A | 2/1995 | Christodoulou et al. |
| 5,396,882 A | 3/1995 | Zapol |
| 5,427,797 A | 6/1995 | Frostell et al. |
| 5,485,827 A | 1/1996 | Zapol et al. |
| 5,500,230 A | 3/1996 | Nathanson |
| 5,525,357 A | 6/1996 | Keefer et al. |

(Continued)

FOREIGN PATENT DOCUMENTS

| | | |
|---|---|---|
| WO | 9400180 A1 | 1/1994 |
| WO | 9422499 A1 | 10/1994 |

(Continued)

OTHER PUBLICATIONS

Hmaer. American Journal of Respiratory and critical care medicine. vol. 162, 2000 paged 328-330.*

(Continued)

*Primary Examiner* — Lakshmi Channavajjala
(74) *Attorney, Agent, or Firm* — Seed IP Law Group PLLC

(57) ABSTRACT

Methods for treating bacterial respiratory tract infections in an individual comprise administering a therapeutic amount of nitrite composition having a pH of less than 7, and in specific embodiments, a pH of about 5.5-6.5, to the individual. The individual may be a pulmonary disease diagnosed individual and/or the infection may be at least in part caused by mucoid mucA mutant *Pseudomonas aeruginosa*.

15 Claims, 13 Drawing Sheets

(56) References Cited

U.S. PATENT DOCUMENTS

| | | |
|---|---|---|
| 5,536,241 A | 7/1996 | Zapol |
| 5,570,683 A | 11/1996 | Zapol |
| 5,648,101 A | 7/1997 | Tawashi |
| 5,650,442 A | 7/1997 | Mitchell et al. |
| 5,683,668 A | 11/1997 | Hrabie et al. |
| 5,713,349 A | 2/1998 | Keaney |
| 5,789,447 A | 8/1998 | Wink, Jr. et al. |
| 5,814,666 A | 9/1998 | Green et al. |
| 5,814,667 A | 9/1998 | Mitchell et al. |
| 5,823,180 A | 10/1998 | Zapol |
| 5,837,736 A | 11/1998 | Mitchell et al. |
| 5,839,433 A | 11/1998 | Higenbottam |
| 5,840,759 A | 11/1998 | Mitchell et al. |
| 5,873,359 A | 2/1999 | Zapol et al. |
| 5,885,621 A | 3/1999 | Head et al. |
| 5,904,938 A | 5/1999 | Zapol et al. |
| 5,958,427 A | 9/1999 | Salzman et al. |
| 5,968,911 A | 10/1999 | Lawson et al. |
| 6,063,407 A | 5/2000 | Zapol et al. |
| 6,083,691 A * | 7/2000 | Deretic et al. ............... 435/6.12 |
| 6,103,275 A | 8/2000 | Seitz et al. |
| 6,187,332 B1 | 2/2001 | Gern et al. |
| 6,197,762 B1 | 3/2001 | Garvey et al. |
| 6,277,891 B1 | 8/2001 | Sanders et al. |
| 6,314,956 B1 | 11/2001 | Stamler et al. |
| 6,358,536 B1 | 3/2002 | Thomas |
| 6,391,895 B1 | 5/2002 | Towart et al. |
| 6,471,978 B1 | 10/2002 | Stamler et al. |
| 6,472,390 B1 | 10/2002 | Stamler et al. |
| 6,476,037 B1 | 11/2002 | Wallace |
| 6,601,580 B1 | 8/2003 | Bloch et al. |
| 6,656,452 B1 | 12/2003 | Zapol et al. |
| 6,709,681 B2 | 3/2004 | Benjamin et al. |
| 6,723,703 B2 | 4/2004 | Gaston et al. |
| 6,811,768 B2 | 11/2004 | Zapol et al. |
| 6,935,334 B2 | 8/2005 | Bloch et al. |
| 6,945,247 B1 | 9/2005 | Stamler et al. |
| 7,040,313 B2 | 5/2006 | Fine et al. |
| 7,048,951 B1 | 5/2006 | Seitz et al. |
| 7,335,183 B2 | 2/2008 | Buiatti |
| 2002/0141597 A1 | 10/2002 | Wilcock |
| 2002/0151597 A1 | 10/2002 | Banerjee et al. |
| 2002/0155174 A1 | 10/2002 | Benjamin et al. |
| 2003/0032917 A1 | 2/2003 | Stamler |
| 2003/0212004 A1 | 11/2003 | Gaston et al. |
| 2004/0013747 A1 | 1/2004 | Tucker et al. |
| 2004/0037897 A1 | 2/2004 | Benjamin et al. |
| 2004/0105898 A1 | 6/2004 | Benjamin et al. |
| 2005/0036949 A1 | 2/2005 | Tucker et al. |
| 2005/0037093 A1 | 2/2005 | Benjamin |
| 2005/0069595 A1 | 3/2005 | Chen et al. |
| 2005/0131064 A1 | 6/2005 | Gaston et al. |
| 2005/0142218 A1 | 6/2005 | Tucker et al. |
| 2006/0147553 A1 | 7/2006 | Miller et al. |
| 2006/0182815 A1 | 8/2006 | Gladwin et al. |
| 2007/0086954 A1 | 4/2007 | Miller |
| 2007/0104653 A1 | 5/2007 | Miller et al. |
| 2007/0144515 A1 | 6/2007 | Stenzler et al. |
| 2007/0154407 A1 | 7/2007 | Peters et al. |
| 2007/0154569 A1 | 7/2007 | Gladwin et al. |
| 2007/0190184 A1 | 8/2007 | Montgomery et al. |

FOREIGN PATENT DOCUMENTS

| | | |
|---|---|---|
| WO | 9522335 | 8/1995 |
| WO | 9902148 A1 | 1/1999 |
| WO | 9938472 | 8/1999 |
| WO | 9944622 | 9/1999 |
| WO | 0030659 A1 | 6/2000 |
| WO | 0110406 A2 | 2/2001 |
| WO | 0126547 A1 | 4/2001 |
| WO | 0143805 A2 | 6/2001 |
| WO | 0180890 A2 | 11/2001 |
| WO | 0189572 | 11/2001 |
| WO | 0189617 A1 | 11/2001 |
| WO | 0217898 A2 | 3/2002 |
| WO | 2005004884 | 1/2005 |
| WO | 2005007173 | 1/2005 |

OTHER PUBLICATIONS

Yoon et al. *P. aeuroginosa* anaerobic respiration in biofilms: relationships to cystic fibrosis pathogenesis. 2002. vol. 3, pp. 593-603.*

Hunter et al. Inhaled nebulized nitrite is a hypoxia-sensitive NO-dependent selective pulmonary vasodilator. Nature Medicine, Oct. 2004, vol. 10 (No. 10), pp. 1122-1127.*

Babcock (Ed.), Webster's Third New International Dictionary of the English Language Unabridged, G. & C. Merriam Company, Springfield, MA, 1963. (2 pages including cover).

Cannon et al., "Effects of inhaled nitric oxide on regional blood flow are consistent with intravascular nitric oxide delivery," The Journal of Clinical Investigation, 108(2):279-287, 2001.

Doyle et al., "Kinetics and Mechanism of the Oxidation of Human Deoxyhemoglobin by Nitrites," The Journal of Biological Chemistry, 256(23):12393-12398, Dec. 10, 1981.

Duriez et al., "A common variant in combination with a nonsense mutation in a member of the thioredoxin family causes primary ciliary dyskinesia," Proceedings of the National Academy of Sciences of the United States of America, 104(9):3336-3341, Feb. 27, 2007.

Fox-Robichaud et al., "Inhaled NO as a Viable Antiadhesive Therapy for Ischemia/Reperfusion Injury of Distal Microvascular Beds," The Journal of Clinical Investigation, 101(11):2497-2505, Jun. 1998.

Gladwin et al., "Pathogenesis and treatment of acute chest syndrome of sickle-cell anaemia," The Lancet, 355 (9214):1476-1478, Apr. 29, 2000.

Guo et al., "Endothelial Preserving Actions of a Nitric Oxide Donor in Carotid Arterial Intimal Injury," Methods and Findings in Experimental and Clinical Pharmacology, 16(5):347-354, 1994.

Henderson et al., "'Hot Dog' Headache: Individual Susceptibility to Nitrite," The Lancet, 2(7788):1162-1163, Dec. 2, 1972.

Hot Dog Nutrition Fatcs, URL=http://www.calorie-count.com/calories/item/21118.html, download date Aug. 25, 2008.

Lauer et al., "Plasma nitrite rather than nitrate reflects regional endothelial nitric oxide synthase activity but lacks intrinsic vasodilator action," Proceedings of the National Academy of Sciences of the United States of America, 98 (22):12814-12819, Oct. 23, 2001.

Lefer, "Myocardial protective actions of nitric oxide donors after myocardial ischemia and reperfusion," New Horizons (Baltimore, MD), 3(1):105-112, Feb. 3, 1995. [Abstract Only].

Lyra et al., "The Importance of Surfactant on the Development of Neonatal Pulmonary Diseases," Clinics (São Paulo, Brazil), 62(2):181-190, 2007.

Nachtsheim, "Sildenafil-A Milestone in the Treatment of Impotence," The Western Journal of Medicine, 169 (2):112-113, Aug. 1998.

Rassaf et al., "Evidence for in vivo transport of bioactive nitric oxide in human plasma," The Journal of Clinical Investigation, 109(9):1241-1248, May 2002.

Zhang et al., "Nitric Oxide Donors Increase Blood Flow and Reduce Brain Damage in Focal Ischemia: Evidence that Nitric Oxide is Beneficial in the Early Stages of Cerebral Ischemia," Journal of Cerebral Blood Flow and Metabolism, 14:217-226, 1994.

Bazylinski, et al., "Growth of *Pseudomonas aeruginosa* on nitrous oxide,". Appl. Environ. Microbiol, 51(6):1239-1246, Jun. 1986.

Carlsson S., et al., "Effects of pH, nitrite, and ascorbic acid on nonenzymatic nitric oxide generation and bacterial growth in urine," Nitric Oxide, 5(6):580-6, Dec. 2001.

Dowling R.B., et al., "Effect of inhibition of nitric oxide synthase on *Pseudomonas aeruginosa* infection of respiratory mucosa in vitro," Am. J. Respir. Cell Mol. Biol., 19(6):950-958, Dec. 1998.

Dukelow, et al., "Effects of nebulized diethylenetetraamine-NONOate in a mouse model of acute *Pseudomonas aeruginosa* pneumonia," Chest, 122(6):2127-2136, Dec. 2002.

Francoeur C., et al. "Nitric oxide and interleukin-8 as inflammatory components of cystic fibrosis," Inflammation, 19(5):587-598, Oct. 1995.

(56) References Cited

OTHER PUBLICATIONS

Grasemann H., "Total sputum nitrate plus nitrite is raised during acute pulmonary infection in cystic fibrosis," Am. J. Respir. Crit. Care. Med., 159(2):684-685, Feb. 1999.

Kalkowski, I., et al. "Metabolism of nitric oxide in denitrifying *Pseudomonas aeruginosa* and nitrate-respiring *Bacillus cereus*," FEMS Microbiol Lett., 66(1):107-111, Jul. 15, 1991. (English Abstract only).

Kelley, T.J., et al., "Inducible nitric oxide synthase expression is reduced in cystic fibrosis murine and human airway epithelial cells," J. Clin. Invest., 15;102(6):1200-1207, Sep. 1998.

Oishi, K, et al., "Nitrite reductase from *Pseudomonas aeruginosa* induces inflammatory cytokines in cultured respiratory cells," Infect. Immun., 65(7):2648-2655, Jul. 1997.

Rake, et al., "Inhibition, but not uncoupling, of respiratory energy coupling of three bacterial species by nitrite," J. Bacteriol. ,144(3):975-982, Dec. 1980.

Saito, S., et al. "Sensitivity of bacteria to NaNO2 and to L-arginine-dependent system in murine macrophages," Microbiol. Immunol., 35(4):325-9, 1991.

Shimada, H. et al., "The pH-dependent reactions of *Pseudomonas aeruginosa* nitrite reductase with nitric oxide and nitrite," J. Biochem, 84(6):1553-8, Dec. 1978.

Webert K.E., et al. "Effects of inhaled nitric oxide in a rat model of *Pseudomonas aeruginosa* pneumonia," Crit. Care. Med. 28(7):2397-2405, Jul. 2000.

Yarbrough J.M. et al., "Bacterial inhibitory effects of nitrite: inhibition of active transport, but not of group translocation, and of intracellular enzymes," Appl Environ Microbiol., 39(4):831-834, Apr. 1980.

Rowe et al., "Nitrite Inhibition of Aerobic Bacteria," *Current Microbiology* 2:51-54, 1979.

Anthony, M., et al., "Genetic analysis of *Pseudomona aeruginosa* isolates from the sputa of Australian adult cystic fibrosis patients," J. Clin. Microbiol. 40(8):2772-2778, Aug. 2002.

Goldberg, J.B., et al., "Cloning and expression in *Pseudomonas aeruginosa* of a gene involved in the production of alginate," J.Bacteriol. 158(3):1115-1121, Jun. 1984.

Hassett, D.J., "Anaerobic production of alginate by *Pseudomonas aeruginosa*: alginate restricts diffusion of oxygen," J. Bacteriol. 178(24):7322-7325, Dec. 1996.

Holloway, B.W. "Genetics of *Pseudomonas*," Bacteriol. Rev. 33(3):419-443, Sep. 1969.

Martin, D.W., et al., "Mechanism of conversion to mucoidy in *Pseudomonas aeruginosa* infecting cystic fibrosis patients," Proc. Natl. Acad. Sci. 90:8377-8381, Sep. 1993.

Worlitzsch, D., et al., "Effects of reduced mucus oxygen concentrations in airway *Pseudomonas* infections of cystic fibrosis patients," J. Clin. Invest. 109(3):317-325, Feb. 2002.

* cited by examiner

METHODS FOR TREATING BACTERIAL RESPIRATORY TRACT INFECTIONS IN AN INDIVIDUAL USING ACIDIFIED NITRITE

FIELD OF THE INVENTION

The present invention is directed to methods for treating bacterial respiratory tract infections in an individual comprising administering a therapeutic amount of nitrite composition having a pH of less than 7, and in specific embodiments, a pH of about 5.5-6.5, to the individual. The individual may be a pulmonary disease diagnosed individual and/or the infection may be at least in part caused by mucoid mucA mutant *Pseudomonas aeruginosa*.

BACKGROUND OF THE INVENTION

Bacterial respiratory tract infections can plague even the most healthy of individuals. Luckily for these healthy individuals, most of the bacterial respiratory tract infections they contract can be successfully treated with conventional antibiotics. There are some pathogens, however, which have proven very difficult to treat in both healthy and sick individuals. In addition to being difficult to treat, many of these pathogens are opportunistic and tend to infect those whose immune systems are already compromised. Three of these opportunist pathogens are *Pseudomonas aeruginosa* (*P. aeruginosa*), *Burkholderia cepacia* (*B. cepacia*), and *Staphylocoocus aureus* (*S. aureus*) (both wild type and methicillin-resistant).

Susceptibility to bacterial respiratory tract infections is especially high for those individuals who are already plagued by a pulmonary disease such as, for example, cancer, black lung, pneumonia (ex. ventilator-associated), bronchiectasis, cystic fibrosis (CF), and chronic obstructive pulmonary disease (COPD). COPD is a collective term that describes ailments associated with airway obstruction. These ailments include, for example, chronic bronchitis, asthma, and emphysema. COPD is the fourth leading cause of death in the U.S. (120,000 deaths in 2002 alone) and is often linked to smoking. *P. aeruginosa*, *B. cepacia*, and *S. aureus* are prevalent in those individuals with COPD and/or CF.

CF is one of the most common fatal genetic disorders in the United States. CF is most prevalent in the Caucasian population and occurs on an average of one in every 3,300 live births. A mutation in a gene that encodes a chloride channel, the cystic fibrosis transmembrane conductance regulator (CFTR), produces partially functional or completely dysfunctional channels. Depending on the mutation and whether the person carries one or two copies of the mutated allele, the prognosis varies widely: heterozygous individuals are asymptomatic for life while those who are homozygous for the mutation have CF. If patients have the most common CF allele, DF508, they typically die by the age of 36.8.

CF patients develop thick mucus secretions resulting from the disruption of the salt/water balance. These mucus secretions clog bronchial tubes in the lungs and plug exit passages of the pancreas and intestines that often lead to a loss of function of these organs. It is in this thick airway mucus, depleted of oxygen by the metabolic activity of aerobic bacteria, neutrophils, and even epithelial cells, where many opportunistic and pathogenic bacteria thrive.

In CF patients, *P. aeruginosa* is one of the most common bacteria trapped in the thickened, dehydrated, hypoxic mucus lining in airway epithelia. Chronic lung infection of CF patients by *P. aeruginosa* is the leading cause of morbidity and mortality associated with the disease. Moreover, while *P. aeruginosa* infections are typically treatable with antibiotics, this bacterium often converts to a mucoid form that is antibiotic-resistant and incapable of reverting to their nonmucoid antibiotic susceptible counterparts. This is particularly true in CF individuals. As *P. aeruginosa*, *B. cepacia*, *S. aureus*, and other pathogens are continuing to cause bacterial respiratory tract infections in both healthy and immunocompromised individuals, a need exists for additional methods of treating these infections.

SUMMARY OF THE INVENTION

Accordingly, the present invention provides methods for treating bacterial respiratory tract infections.

In accordance with one aspect of the invention, a method for treating an individual with a bacterial respiratory tract infection caused at least, in part, by the mucoid form of *P. aeruginosa* is provided. The method comprises administering a nitrite composition at a pH of less than 7 to affected individuals.

In accordance with yet another aspect of the invention, a method for treating a bacterial respiratory tract infection in an individual diagnosed with Cystic Fibrosis is provided. The method comprises administering a nitrite composition having a pH of less than 7 to the individual diagnosed with Cystic Fibrosis.

In accordance with another aspect of the invention, a method for treating a bacterial respiratory tract infection in an individual diagnosed with chronic obstructive pulmonary disease is provided. The method comprises administering a nitrite composition having a pH of less than 7 to infected individuals.

In accordance with yet another aspect, a method for treating a bacterial respiratory tract infection caused at least in part by *Staphylococcus aureus* in an individual is provided. The method comprises administering a therapeutic amount of nitrite composition having a pH of less than 7 to the individual.

Additional embodiments, objects and advantages of the invention will become more fully apparent in light of the detailed description below.

BRIEF DESCRIPTION OF THE DRAWINGS

The following detailed description will be more fully understood in view of the accompanying drawings in which:

FIG. 1 shows the results when FRD1 and FRD1 of the non-mucoid type are incubated together at the indicated ratios for five days in the presence of 15 mM $NO_2^-$, pH of 6.5, after which CFU are determined. The black bars indicate non-mucoid FRD1/pmucA and the gray bars indicate mucoid FRD1.

Figure 1:
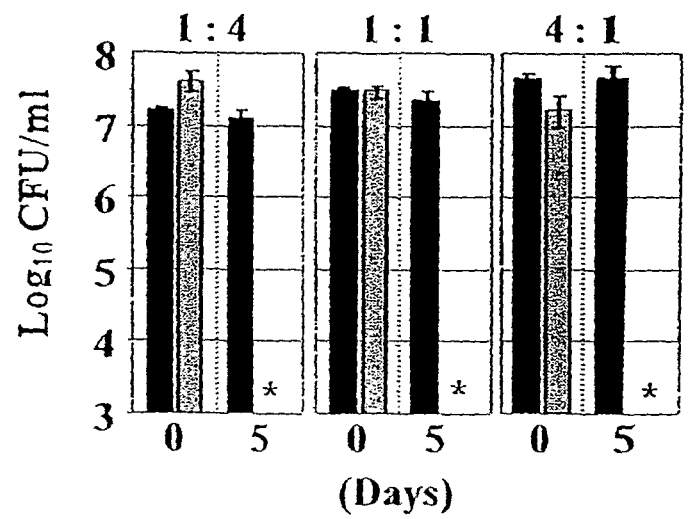
FIG. 1 shows that mucoid *P. aeruginosa* FRD1 is selectively killed by $NO_2^-$ at a pH of 6.5.

The embodiments set forth in the drawings are illustrative in nature and are not intended to be limiting of the invention defined by the claims. Moreover, individual features of the drawings and the invention will be more fully apparent and understood in view of the following detailed description.

DETAILED DESCRIPTION OF THE INVENTION

The present invention is directed to methods for treating bacterial respiratory tract infections in an individual by administering a therapeutic amount of nitrite composition having a pH of less than 7 to the individual.

Currently, the most common treatment administered for a bacterial respiratory tract infection is one or more antibiotics. There are, however, bacterial respiratory tract infections that are refractory to antibiotics due to inherent resistance mechanisms of the infecting organisms. These include, for example, resistance developed by acquiring genes involved in antibiotic efflux or penetration difficulties based on the current condition of the host's body. As such, new treatments are required to combat bacterial respiratory tract infections that can be used on their own, in combination with antibiotics, or in combination with other medications.

Compounding some of the treatment difficulties mentioned above, many bacteria are also opportunistic, primarily afflicting those individuals whose immune systems have already been compromised. While some individuals have difficulty fighting off infection due to decreased immune response, others have difficulty fighting off infection due to effects on their body from disease.

For instance, CF and COPD patients have the necessary biological responses to fight off infections, however, these responses are compromised when the biological response cannot reach the bacteria because the bacteria is lodged in the mucous linings of the lungs. For these individuals, a difficult to treat bacterial respiratory tract infection can be life threatening. For example, *Pseudomonas aeruginosa, Burkholderia cepacia*, and *Staphylococcus aureus* bacteria are prevalent in the airways of both Cystic Fibrosis and COPD patients where they flourish in the thickened mucus lining of their lungs. Chronic infections caused by these bacteria due to the inability to treat them effectively are the leading cause of morbidity and mortality associated with CF.

More specifically, *Staphylococcus aureus* bacteria, especially the methicillin-resistant variant (MRSA), have become a monumental problem due to their ability to acquire resistance to the most common antibiotic used against them (methicillin). The current last resort for treatment against these antibiotic resistant strains is with vancomycin. However, there are currently strains which exhibit resistance to this treatment as well. Surprisingly, these bacteria exhibited susceptibility to slightly acidified nitrite. Thus, nitrite could be used to treat *Staphylococcus aureus* infections, including but not limited to those in the respiratory tract.

Turning to *P. aeruginosa*, recent studies indicate that (PA) grows anaerobically as biofilms in the thick, stagnant mucus lining the CF airway lumen. The anaerobic nature of the CF airway mucus reflects the collective oxygen consumptive activities of (i) airway epithelia, (ii) PA and other opportunistic pathogens, and (iii) neutrophils that combat infection. As CF lung disease progresses, mucoid, alginate-overproducing strains emerge and become the predominant form of PA during chronic infection. Mucoid PA biofilms are inherently resistant to antibiotics and phagocytic neutrophils. The best characterized mechanism of mucoid conversion in CF isolates is via mutations in mucA, a gene encoding a cytoplasmic membrane spanning anti-sigma factor (1). Without mucA, the sigma factor AlgT(U) transcribes alginate biosynthetic genes. Mutations in mucA and mucoid conversion can be triggered in vitro when biofilms are treated with $H_2O_2$ at levels similar to those generated by human neutrophils. Studies have reported that approximately 84% of mucoid CF isolates (n=53) in America possess mutations in the mucA gene while mucoid mucA mutant bacteria are found in ~44% of CF isolates from an Australian study (2).

An important link between mucoidy and anaerobic metabolism by PA was made in 1996; mucoid organisms were found to be incapable of reversion to their nonmucoid, antibiotic- and phagocyte-susceptible counterparts during anaerobic growth (3). In addition, after the switch to anaerobic growth metabolism, typical bacterial infection treatments, like tobramycin, have a decreased efficacy. Recent reports indicate that anaerobic airway surface liquid favored the production of alginate by PA. (4). PA is capable of robust anaerobic growth by respiration using nitrate ($NO_3^-$) or, to a lesser extent, nitrite ($NO_2^-$) as terminal electron acceptors. $NO_3^-$ and $NO_2^-$ are present in CF airway surface liquid and CF sputum, which could allow anaerobic growth of PA. Still, during anaerobic growth, PA must control the levels of a toxic gaseous by-product of $NO_2^-$ reduction, nitric oxide (NO), by synthesis of the protective enzyme NO reductase (NOR).

The necessity of PA to detoxify NO to survive was also demonstrated by the observation that overproduction of NO by anaerobic PA biofilms lacking the rhl quorum sensing circuit caused death of these bacteria. NO is also produced in normal airway epithelia by inducible NO synthesis (iNOS) that contributes to antimicrobial defense of the airway. The rhl quorum sensing circuit allows the bacterial to talk to each other at high cell density (i.e. biofilms). So, when the rhlR gene is inactivated, the organisms change their metabolism so that it overproduces endogenous NO. In effect, the organisms commit metabolic suicide. In addition, in chronic CF, iNOS activity (which produces endogenous NO) is significantly reduced, and this defect is likely to contribute to the persistence of PA infections.

Thus, the ability of PA to grow anaerobically with nitrite ($NO_2^-$) as a terminal electron acceptor depends on its ability to remove toxic NO gas. Nitrite at the acidic pH of the CF airways results in increased $HNO_2$ which, in turn, results in increased NO accumulation. This increase in NO production from nitrite at acidic pH leads to bacterial death, making nitrite an effective therapeutic for CF patients with mucoid PA infections.

Accordingly, the present invention is directed toward novel methods for treatment of bacterial respiratory tract infections. In one particular embodiment, the inventive methods are suitable for treatment of respiratory tract infections in individuals diagnosed with CF. In additional embodiments, a method according to the present invention is directed to treatment of a bacterial respiratory tract infection caused at least in part by *Pseudomonas aeruginosa* of a mucoid type and/or *Staphylococcus aureus*. In further embodiments, a method according to the invention is for treating such an infection in an individual diagnosed with pulmonary disease. In another embodiment, a method according to the invention is for treating a bacterial respiratory tract infection in an individual diagnosed with chronic obstructive pulmonary disease.

The methods according to the present invention comprise administering a therapeutic amount of nitrite composition, for example in a solution form, having a pH of less than 7 to the individual. In more specific embodiments, the nitrite composition has a pH of about 5.5-6.5, has a pH of about 6.5, or has a pH of about 5.5.

The nitrite may be administered to the individual via any suitable route or device. In one embodiment, the nitrite is administered via a nebulizer (an inhaler). The most common form of delivery will be as a mist. This method of delivery allows better penetration of the solution to the bacteria embedded in the biofilm as compared to a gas. Aerosol delivery systems typically contain concentrations of a nebulized agent that are ~25-fold higher than the effective killing dose in airway surface liquid (ASL). In another embodiment, the nitrite is administered in dry powder form via crushed powder delivery systems. In another embodiment, the nitrite composition is administered as NO gas. The most common form of delivery for the powder and the gas is also through inhalation.

The nitrite composition is administered in an amount sufficient to treat the bacterial respiratory tract infection. The treatment as used herein encompasses a reduction in clinical symptoms of the infection and/or elimination of the bacteria causing the infection. Therapeutic amounts will vary based on an individual's age, body weight, symptoms and the like, and may be determined by one of ordinary skill in the art in view of the present disclosure. In one embodiment, the therapeutic amount of nitrite composition is sufficient to allow at least about 3 mM of nitrite to reach the bacterial respiratory tract infection site. In one embodiment, 3 mM $NO_2^-$ can typically generate sufficient NO to kill 50% of the mucA mutant PA in the CF airways while 15 mM $NO_2^-$ can typically kill approximately 100%, even in the absence of or reduced expression of human iNOS. Thus, for treatment of mucoid, mucA mutant PA, the aerosol theoretically may, in one embodiment, contain about 375 mM $NO_2^-$ at about pH 6.5 (or lower) to deliver about 15 mM $NO_2^-$ to CF ASL. Acidified $NO_2^-$ delivered in such doses to the CF ASL will kill mucoid PA without harming airway epithelia or disrupting key physiological lung functions.

The methods according to the present invention are particularly suitable for treating a bacterial respiratory tract infection in a CF individual caused by *Pseudomonas aeruginosa, Burkholderia cepacia*. and/or *Staphylococcus aureus* types. In additional embodiments, the methods according to the invention are suitable for treating bacterial respiratory infection caused by *Pseudomonas aeruginosa* of a mucoid type. A mucoid *Pseudomonas aeruginosa* is defined as an organism that overproduces the exopolysaccharide alginate. The production of alginate severely complicates the overall clinical course for CF patients and renders such organisms resistant to phagocytic cells and antibiotics.

A study to determine whether killing by $NO_2^-$ is selective for mucoid bacteria, is illustrated in FIG. 1, which shows CFU concentrations for mucoid (gray bar graph) and nonmucoid (black bar graph) PA. Mucoid and nonmucoid PA are mixed and treated with anaerobic 15 mM $NO_2^-$, pH of 6.5, after which CFU are measured. After 5 days, mucoid FRD1 consistently loses viability at three different bacterial ratios tested (*=<$10^3$ CFU/ml), while nonmucoid FRD1/pmucA maintains viability.

Figure 2:
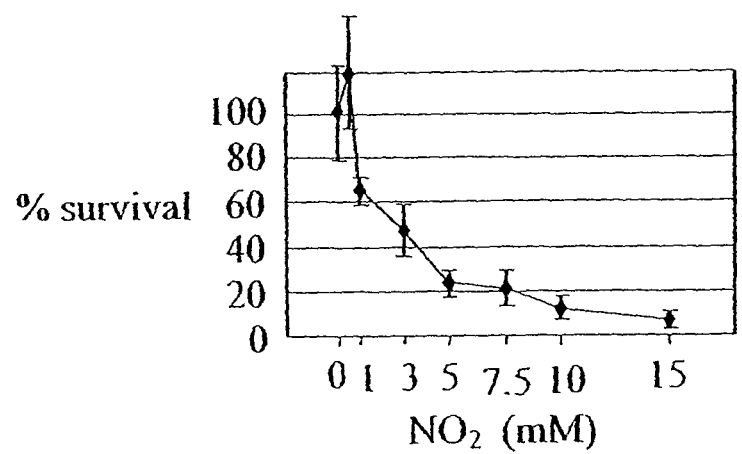
FIG. 2 sets forth a dose response curve of treating mucoid FRD1 by $NO_2^-$, pH of 6.5, wherein bacteria are suspended in L-broth (pH of 6.5) with various amounts of $NO_2^-$ for 24 hours under anaerobic conditions. The survival against $NO_2^-$ is presented as the percentage of CFU relevant to that in the initial inoculum.
Figure 3:
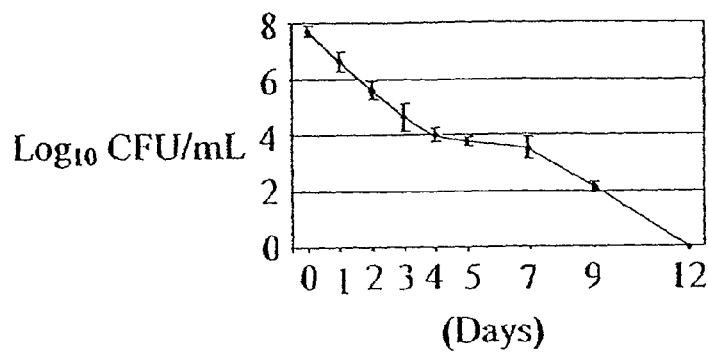
FIG. 3 shows the long-term effect of anaerobic exposure of the mucoid strain FRD1 to 15 mM $NO_2^-$ at a pH of 6.5.

Dose-effect relationships between the $NO_2^-$ concentration and killing of mucoid bacteria is demonstrated in FIG. 2. Ninety to ninety-five percent of the bacteria are killed by 15 mM $NO_2^-$, pH of 6.5, and the $LD_{50}$ is ~3 mM $NO_2^-$ after a 24 hr. period. The survival against $NO_2^-$ is presented as a percentage of CFU relevant to that in the initial inoculum. As shown in FIG. 3, remaining organisms cannot develop resistance to $NO_2^-$, pH of 6.5, when the study is extended to 12 days, demonstrating that all organisms are killed during this time.

Thus, $NO_2^-$ is an effective therapeutic agent against mucoid PA if the pH of CF airway surface liquid is slightly acidic. Previous in vitro studies suggest that the pH of the CF airway surface liquid is <6.5. However, the pH of mucopurulent secretions within CF airways can differ in vivo. In situ pH measurements of luminal secretions from freshly explanted lungs removed from 9 CF patients at the time of transplantation have shown the pH of the secretions may indeed be lower than in vitro: for example, 6.45+/−0.03 in segmental airways and even lower in more distal subsegmental bronchi (6.39+/−0.04).

Figure 4:
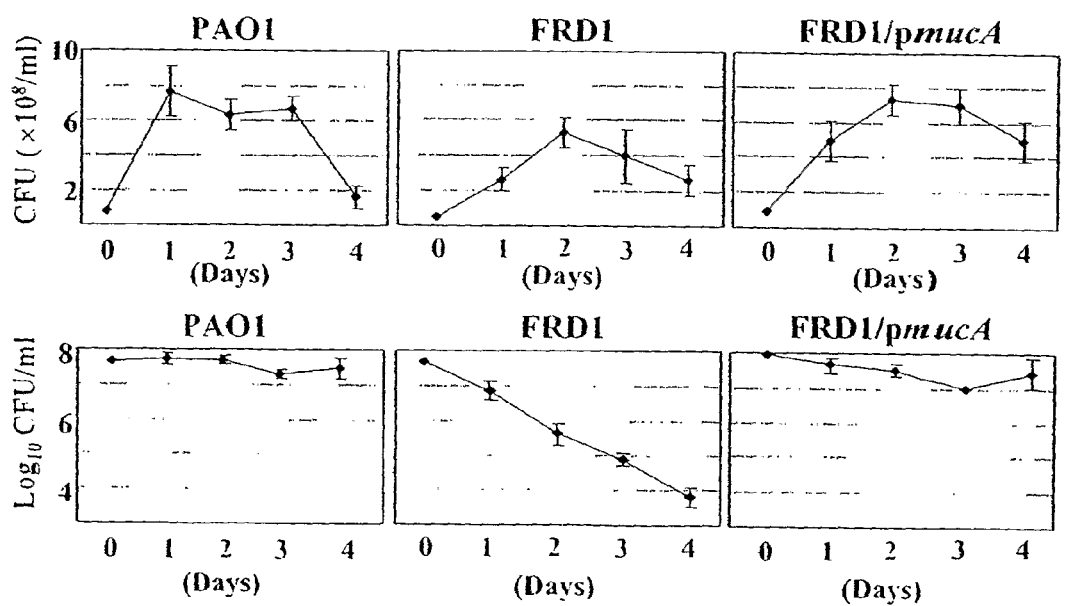
FIG. 4 shows the differential effect of nitrite at pH 6.5 on mucoid and non-mucoid PA strains. Aerobic overnight suspensions of non-mucoid PA01, mucoid FRD1, and non-mucoid FRD1/pmucA are diluted 100 fold for the main anaerobic culture with $NO_3^-$ (top) or $NO_2^-$ (bottom). The colony forming units (CFU) are enumerated each day and plotted.

Based upon the slightly acidic pH measurements of segmental and subsegmental bronchi from CF transplant patients, discussed above, well-characterized *P. aeruginosa* strains are grown at pH 6.5 under strict anaerobic conditions. Thus, upon anaerobic culture of PA at pH 6.5 with 15 mM $NO_3^-$ (electron acceptor), mucoid PA strain FRD1 grew more slowly than nonmucoid PAO1 and FRD1/pmucA. Strain FRD1 is the best characterized mucoid, mucA mutant derived from a CF patient. However, no difference in viability patterns is observed (FIG. 4). Using 15 mM $NO_2^-$, however, mucoid FRD1 is killed at a rate of 90% per day, while two nonmucoid strains, PAO1 and FRD1/pmucA, remained viable over the 4 day incubation (FIG. 4).

Figure 7:
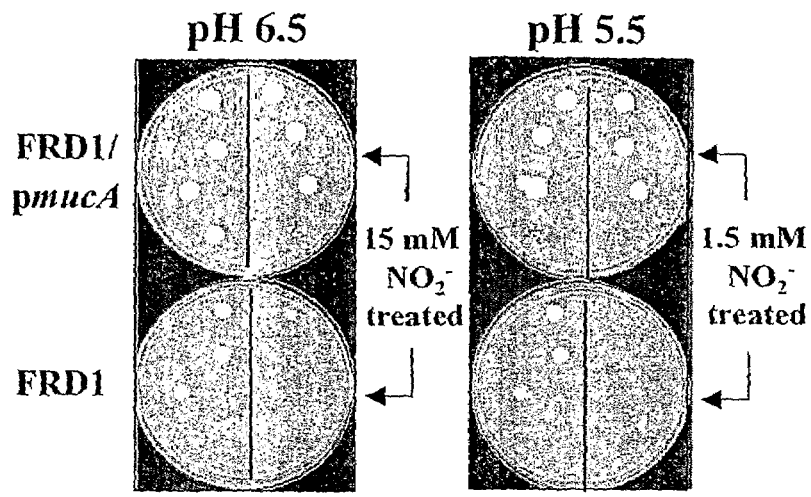
FIG. 7 shows the anaerobic sensitivity of mucoid FRD1 and non-mucoid FRD1/pmucA under conditions allowing for identical NO levels to be produced. Bacteria are incubated anaerobically for 4 days with or without 15 mM and 1.5 mM $NO_2^-$ at pH 6.5 and 5.5, respectively. To enumerate viable cells, 10 µl suspensions of $10^{-1}$ through $10^{-4}$ serial dilutions are spotted on LB agar plates and incubated at 37° C. under aerobic conditions for 15 hr. The left and right side of each plate represent control and $NO_2^-$ exposed bacteria.

Collectively, the acidic pH of the CF airway mucus promotes the generation of toxic $NO_2^-$ derivative(s) that selectively kill mucA mutant PA. These species originate from nitrous acid ($HNO_2$, $pK_a$=3.35), whose equilibrium concentration increases exponentially with medium acidity; at pH 6.5 and 15 mM $NO_2^-$, the $HNO_2$ concentration is 10.62 µM. Exposure of Strain FRD1 to two different culture conditions that generate identical $HNO_2$ concentrations (pH 6.5/15 mM $NO_2$ and pH 5.5/1.5 mM $NO_2^-$) results in equal killing of mucoid bacteria. Both mucoid FRD1 and nonmucoid FRD1/pmucA maintain viability at pH 6.5 and 5.5 except when $NO_2^-$ is added (FIG. 7).

Figure 5:
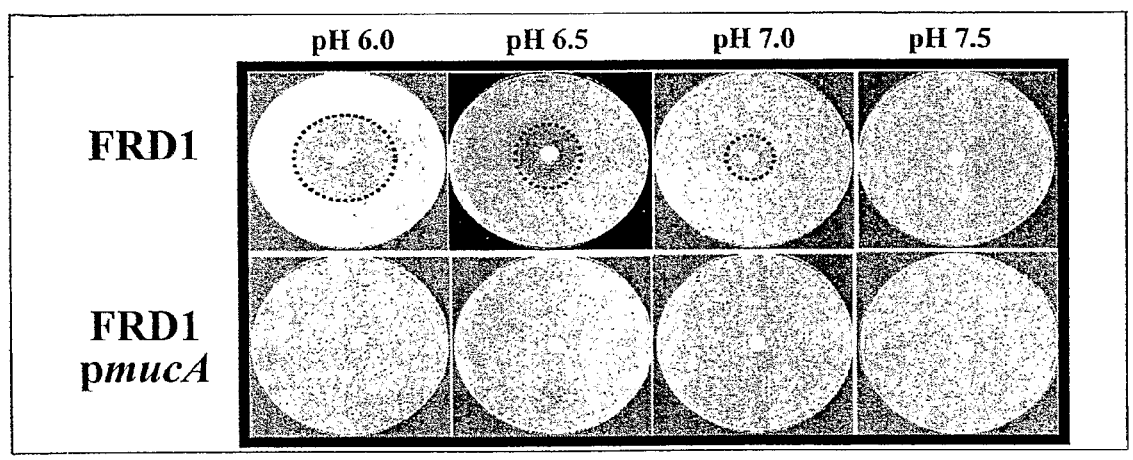
FIG. 5 shows the $NO_2^-$ sensitivity versus pH of FRD1 and FRD1/pmucA. The FRD1 and FRD1/pmucA are seeded on LB agar and buffered at the indicated pH. After placing a filter disc containing 10 µl of 1 M $NO_2^-$, the plates are incubated anaerobically for 48 hours and scanned for an observable zone of killing.

After discovering this unique $NO_2^-$ sensitivity of mucA mutant strain FRD1, it was also found that $NO_2^-$ killed these bacteria more effectively at lower pH (FIG. 5) while little or no killing is observed in strain FRD1/pmucA at pH values between 6.0 and 7.5 (FIG. 5).

Figure 6:
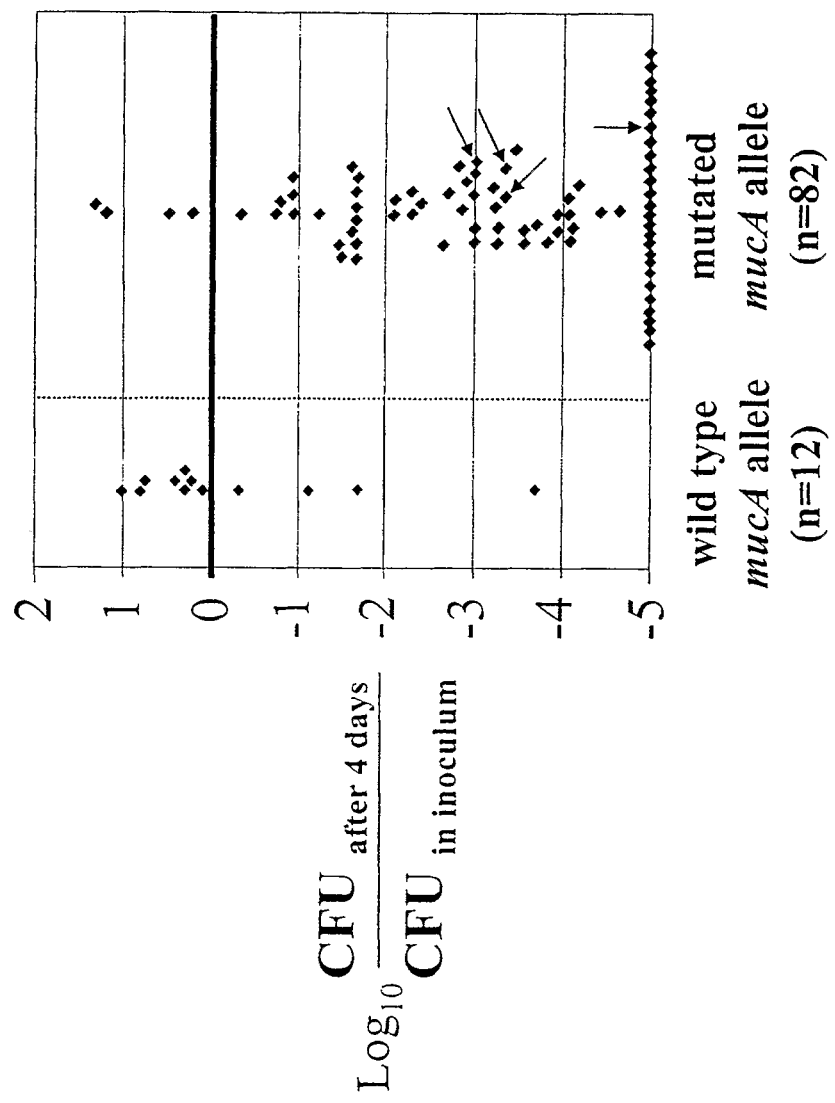
FIG. 6 shows the $HNO_2$ sensitivity of 94 different mucoid CF clinical isolates of PA. Aerobic starter cultures of each strain are diluted 100-fold in LB (pH 6.5) supplemented with 15 mM $NO_2^-$. The CFU in the inoculum versus that after a 4 day anaerobic incubation are determined. The mucA gene of each isolate is sequenced and mucoid strains with wild-type mucA alleles and those harboring mucA mutation are shown in the left and right side of the graph, respectively. The black arrows indicate clinical isolates that are found to be highly resistant to amikacin, aztreonam, cefepime, ceftazidime, ciprofloxacin, gentamycin, imipenem and tobramycin.

In addition, other mucoid, mucA mutant CF isolates are also sensitive to $NO_2^-$. To test whether $NO_2^-$ sensitivity is a trait of all mucA mutant mucoid CF isolates, the mucA genes of 94 mucoid clinical isolates recovered from a variety of CF clinics in the United States and Canada are sequenced. Of 94 strains, 82 harbored mucA mutations, leading to either premature termination of translation (88%) or a loss of the stop codon (12%), thereby confirming previous findings that mucA mutations are the major reason for mucoid conversion in CF isolates (FIG. 6 and Table 1). The most abundant mutations are single base pair deletions that result in a frame shift leading to premature termination of translation at base pair 441 (the wild type mucA gene is 585-bp). Approximately 13% of mucoid isolates have a wild-type mucA allele, indicating the presence of other mechanisms or mutations allowing for mucoid conversion. Upon anaerobic treatment with 15 mM $NO_2^-$ at pH 6.5, almost all of the mucA mutant mucoid isolates (78 out of 82 strains) show increased susceptibility to $NO_2^-$, with 74% killed by more than 2 logs (FIG. 6). Importantly, 4 strains that were deemed antibiotic-resistant are still sensitive to anaerobic treatment of acidified $NO_2^-$ (black arrows in FIG. 6). Out of 12, however, 8 mucoid isolates with a wild-type mucA allele are resistant to acidified $NO_2^-$. These results suggest that $NO_2^-$ sensitivity is likely caused by mucA mutations.

TABLE 1

| Clinic Location | mucA mutation | mutation type | Log10 [CFU in 4 days/CFU in inoculum] | Patient age |
|---|---|---|---|---|
| Seattle | Yes | stop at 441 | −2.15 | N/A |
| Seattle | Yes | stop at 369 | −1 | N/A |
| Seattle | Yes | stop at 387 | −0.3 | N/A |
| Seattle | No | | 0.3 | N/A |
| Wichita | Yes | stop at 351 | −2.52 | N/A |
| Cleveland | Yes | stop at 351 | −4 | N/A |
| Kansas city | Yes | stop at 387 | <−5 | N/A |
| San Francisco | Yes | stop at 426 | −3.52 | N/A |
| Jackson | Yes | stop at 441 | −4.7 | N/A |
| Omaha | Yes | stop at 351 | <−5 | N/A |
| Boston | Yes | stop at 480 | <−5 | N/A |
| Gainsville | Yes | stop at 441 | <−5 | N/A |
| Gainsville | Yes | stop at 426 | −0.53 | N/A |
| Gainsville | Yes | No stop codon, 4 bp insertion | −4.22 | N/A |
| Columbia U. | Yes | stop at 369 | −4.1 | 21 |
| Columbia U. | Yes | stop at 387 | <−5 | 20 |
| Columbia U. | Yes | stop at 354 | −4.52 | 20 |
| Columbia U. | Yes | stop at 351 | −3.53 | 25 |
| Columbia U. | N/D | | <−5 | 63 |
| Columbia U. | No | | −1.69 | 34 |
| Columbia U. | Yes | stopat 342 | −2.54 | 27 |
| Columbia U. | Yes | No stop codon, 127 bp deletion | <−5 | 59 |
| Columbia U. | No | | −3.7 | 39 |
| Columbia U. | Yes | stop at 354 | <−5 | 22 |
| Columbia U. | Yes | stop at 441 | −1.523 | 22 |
| Columbia U. | Yes | stop at 423 | <−5 | 20 |
| Columbia U. | Yes | stop at 291, 5 bp insertion | −1.52 | 28 |
| Columbia U. | Yes | stop at 354 | <−5 | 25 |
| Columbia U. | Yes | stop at 387 | <−5 | 14 |
| Columbia U. | Yes | stop at 441 | <−5 | 36 |
| Columbia U. | Yes | stop at 441 | <−5 | 45 |
| Columbia U. | Yes | stop at 387 | −3.3 | N/A |
| Columbia U. | Yes | stop at 120 | −3.5 | N/A |
| Columbia U. | Yes | stop at 120 | −2 | N/A |
| Columbia U. | Yes | stop at 387 | −3 | N/A |
| Columbia U. | Yes | stop at 288, 2 bp insertion | −3.3 | N/A |
| Columbia U. | Yes | stop at 330 | −3.78 | N/A |
| Columbia U. | Yes | stop at 387 | −3.18 | N/A |
| Columbia U. | Yes | stop at 441 | −3.9 | N/A |
| Columbia U. | Yes | stop at 354 | −3.3 | N/A |
| Columbia U. | Yes | No stop codon, 23 bp insertion | −2.15 | N/A |
| Columbia U. | Yes | stop at 441 | −3.6 | N/A |
| Columbia U. | Yes | stop at 387 | −3.48 | N/A |
| Columbia U. | Yes | No stop codon, 46 bp deletion | −1.35 | N/A |
| Columbia U. | Yes | stop at 285 | −3.6 | N/A |
| Columbia U. | Yes | stop at 441 | −2.7 | N/A |
| Columbia U. | Yes | No stop codon | −3.7 | N/A |
| Columbia U. | No | | −0.31 | N/A |
| CH Boston | Yes | stop at 441 | <−5 | 26 |
| CH Boston | Yes | stop at 369 | −3.22 | 45 |
| CH Boston | Yes | No stop codon | <−5 | 24 |
| CH Boston | Yes | stop at 441 | −3.3 | 39 |
| CH Boston | Yes | stop at 351 | −2.11 | 11 |
| CH Boston | Yes | stop at 396, 45 bp deletion | −3.15 | 37 |
| CH Boston | No | | −1.12 | 27 |
| CH Boston | Yes | stop at 483, 7 bp insertion | <−5 | 20 |
| CH Boston | Yes | stop at 441 | −2.15 | 50 |
| CH Boston | Yes | stop at 378, 100 bp deletion | <−5 | 25 |
| CH Boston | Yes | stop at 441 | −1.39 | 7 |
| CH Boston | Yes | stop at 426 | −1.78 | 13 |
| CH Boston | Yes | stop at 369 | <−5 | 56 |
| CH Boston | Yes | stop at 285 | −3.05 | 23 |

TABLE 1-continued

| Clinic Location | mucA mutation | mutation type | Log10 [CFU in 4 days/CFU in inoculum] | Patient age |
|---|---|---|---|---|
| CH Boston | Yes | stop at 441 | −1.52 | 6 |
| CH Boston | Yes | stop at 354 | −3.3 | 29 |
| CH Cincinnati | No | | 0.75 | N/A |
| CH Cincinnati | Yes | stop at 441 | <−5 | N/A |
| CH Cincinnati | Yes | stop at 384 | −2.15 | N/A |
| CH Cincinnati | No | | 1.01 | N/A |
| CH Cincinnati | Yes | stop at 441 | −3.78 | N/A |
| CH Cincinnati | No | | 0.41 | N/A |
| CH Cincinnati | Yes | stop at 369 | −4.25 | N/A |
| CH Cincinnati | Yes | stop at 369 | −1.98 | N/A |
| CH Cincinnati | Yes | stop at 441 | −2.79 | N/A |
| CH Cincinnati | Yes | stop at 426 | <−5 | N/A |
| CH Cincinnati | No | | 0.23 | N/A |
| CH Cincinnati | Yes | stop at 438 | −2.15 | N/A |
| CH Cincinnati | Yes | No stop codon, 20 bp deletion | <−5 | N/A |
| CH Cincinnati | Yes | stop at 441 | −4.21 | N/A |
| CH Cincinnati | Yes | stop at 441 | <−5 | N/A |
| CH Cincinnati | Yes | No stop codon, 2 bp insertion | <−5 | N/A |
| CH Cincinnati | Yes | stop at 285 | <−5 | N/A |
| CH Cincinnati | Yes | stop at 384 | −2.17 | N/A |
| UBC | Yes | No stop codon, 4 bp deletion | −4.10 | 13.7 |
| UBC | Yes | stop at 387 | 0.3 | 3.4 |
| UBC | Yes | No stop codon, 5 bp insertion | <−5 | 11.8 |
| UBC | Yes | stop at 441 | −4.2 | 16.3 |
| UBC | No | | 0.8 | 15 |
| UBC | Yes | stop at 354 | −4.3 | 6.5 |
| UBC | No | | 0.3 | 5.5 |
| UBC | Yes | stop at 441 | −2.1 | 9.3 |
| UBC | Yes | stop at 369 | −2.7 | 9.7 |
| UBC | Yes | stop at 441 | <−5 | 9.9 |
| UBC | No | | 0.1 | 9.6 |
| UBC | Yes | stop at 441 | 0.41 | 7.7 |

In a separate longitudinal study using PA strains isolated from 5 different young CF patients, mucoid PA is consistently detected as the patient ages, a hallmark of chronic infection (Table 2). As predicted, initial airway colonization of each patient is by nonmucoid PA. Most importantly, however, mucoid variants are detected in patients A, B, C and D possess mutated mucA genes and are all killed by 15 mM $NO_2^-$ (1.9-3.1 logs). These results indicate that the genotypic and phenotypic switch to the mucoid form that is sensitive to $NO_2^-$ treatment can occur in patients less than 3 years of age (see patient C).

TABLE 2

| Patient | Age | Mucoid | mucA mutation | Viability index | Note |
|---|---|---|---|---|---|
| A | 2.8 | NM | No | 0.72 | First PA colonization |
|   | 4.5 | NM | No | 0.13 | |
|   | 6.0 | M | Yes, stop at 441 | −3.1 | First mucoid PA isolation |
| B | 1.2 | NM | No | 0.21 | First PA colonization |
|   | 3.0 | NM | No | 1.07 | |
|   | 5.3 | M | No | −3.14 | First mucoid PA isolation |
|   | 5.5 | M | Yes, stop at 351 | −2.93 | Mucoid PA isolation |
| C | 0.5 | NM | No | 1.3 | First PA colonization |
|   | 2.5 | NM | No | 0.15 | |
|   | 2.9 | M | Yes, stop at 441 | −1.9 | First mucoid PA isolation |
| D | 6.0 | NM | No | 0.13 | First PA colonization |
|   | 7.6 | NM | No | 1.13 | |
|   | 10.7 | M | Yes, stop at 441 | −2.88 | First mucoid PA isolation |

TABLE 2-continued

| Patient | Age | Mucoid | mucA mutation | Viability index | Note |
|---|---|---|---|---|---|
| E | 2.2 | NM | No | 1.2 | First PA colonization |
|  | 5.3 | NM | No | 1.09 |  |
|  | 5.7 | M | No | 0.9 | First mucoid PA isolation |

The above results show that mucA mutations are likely responsible for the enhanced sensitivity to $NO_2^-$. Since mucA mutant bacteria overproduce alginate, experiments are conducted to test whether $NO_2^-$ sensitivity is caused by mucA mutations. An isogenic PAO1 mucA mutant, PDO300, whose intact mucA allele is replaced with that of strain FRD1 (mucA22) is also sensitive to $NO_2^-$ (Table 3). Two FRD1 derived nonmucoid mutants [ΔalgD (lacking GDP-mannose dehydrogenase) and ΔalgT(U), (lacking AlgT(U))] are equally sensitive to killing by $NO_2^-$ (Table 3). It is also tested as to whether $NO_2^-$ also killed mucB, mucD, and algW mutants of strain PAO1. Other than mucA, the aforementioned genes are the only reported loci that, when inactivated, allow for mucoid conversion in PA (25-27). In contrast to mucA mutant bacteria, these mutants are not sensitive to $NO_2^-$ (Table 3). Therefore, our results show that $NO_2^-$ sensitivity is MucA- and not alginate-dependent. Finally, the $LD_{50}$ of $NO_2$ for sensitive strains is almost identical to that for FRD1 (FIGS. 1-5), suggesting that the rate at which these organisms are killed by $NO_2^-$ is similar to that of strain FRD1.

TABLE 3

| Strains | Mucoid | mucA mutation | Viability index | $LD_{50}$ |
|---|---|---|---|---|
| PDO300 (PAO1 mucA22) | M | Yes | −2.4 | 4.1 (±0.2) |
| PAO1 mucB::Tc$^r$ | M | No | 0.45 | N/A |
| PAO1 mucD::Tc$^r$ | M | No | 0.39 | N/A |
| PAO1 algW::Tc$^r$ | M | No | 0.57 | N/A |
| FRD1* | NM | Yes | −3.84 | 2.8 (±0.18) |
| FRD1 algD::Tn501 | NM | Yes | <−3.48 | 2.5 (±0.1) |
| FRD1 algT(U)::Tn501 | NM | Yes | −3.95 | 2.45 (±0.15) |
| Clinical isolate #35* | NM | Yes | <−3.71 | 3.1 (±0.08) |
| Clinical isolate #37* | NM | Yes | <−4.12 | 2.2 (±0.1) |
| Clinical isolate #38* | NM | Yes | <−4.54 | 2.55 (±0.34) |
| Clinical isolate #40* | NM | Yes | <−3.87 | 2.6 (±0.2) |

$HNO_2$ is required for killing of mucA mutant bacteria, but NO and other $HNO_2$-derived intermediates are responsible. Collectively, the results show that the acidic pH ~6.5 of the CF airway mucus promotes the generation of $NO_2^-$ derivative(s) that selectively kill mucA mutant *P. aeruginosa*. Undoubtedly, these derivatives originate from nitrous acid ($HNO_2$, $pK_a$=3.3), whose equilibrium concentration increases with medium acidity. For example, FRD1 is exposed to two different culture conditions with identical $HNO_2$ concentrations of ~10 μM (pH 6.5/15 mM $NO_2^-$ and pH 5.5/1.5 mM $NO_2^-$). Under both conditions, equal killing of bacteria is observed, supporting the notion that formation of $HNO_2$ is a prerequisite for killing mucoid *P. aeruginosa* (FIG. 7). Both mucoid FRD1 and nonmucoid FRD1/pmucA maintain viability at these pH values when no $NO_2^-$ is added (FIG. 7).

Figure 8:
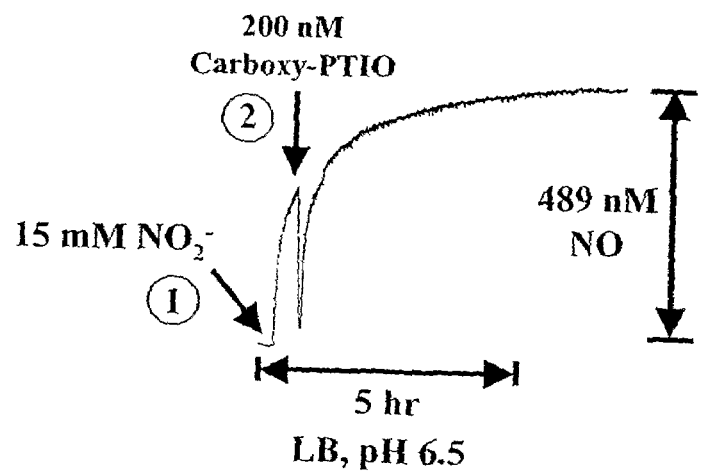
FIG. 8 shows the measurement of NO generated by 15 mM $NO_2^-$ at pH 6.5 using an NO specific electrode. The graph depicting the NO signal generated over time based upon the addition of $NO_2^-$ to LB, pH 6.5 (arrow #1) is shown. The NO scavenger, carboxy-PTIO (200 nM), is added at the position of the arrow #2 and the stoichiometric decrease in NO signal is shown. The coefficient of determination ($r^2$) between NO concentration and electric current (pA) is 0.9997.

Though capable of penetrating membranes, $HNO_2$ is unlikely to directly inflict lethal lesions because it is relatively nonreactive, and should rapidly revert to $NO_2^-$ upon entry into the neutral cytosol. However, $HNO_2$ is unstable toward dismutation that generates a pair of NO and $.NO_2$ radicals. The latter is rapidly removed by dimerization and hydrolysis, but NO persists and, moreover, continuously accumulates (FIG. 8). This complex chemistry is amenable to a kinetic analysis revealing that, while NO reaches concentrations of ~100 nM in ~5 hr in 15 mM $NO_2^-$ (pH 6.5), the $.NO_2$. radical level remains below 0.1 nM. At pH 7.5, about 500-fold less NO is produced over the same period.

Figure 9:
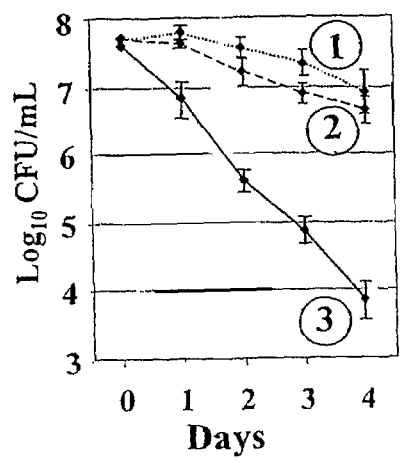
FIG. 9 shows the effects of NO scavengers on protection of mucoid FRD1 from killing by acidified $NO_2^-$. Carboxy-PTIO (5 mM, line 1) or deoxyhemoglobin (0.5 mM, line 2) is added in the initial media (LB, pH 6.5, 15 mM $NO_2^-$). Line 3 is the FRD1 control bacteria alone.
Figure 10:
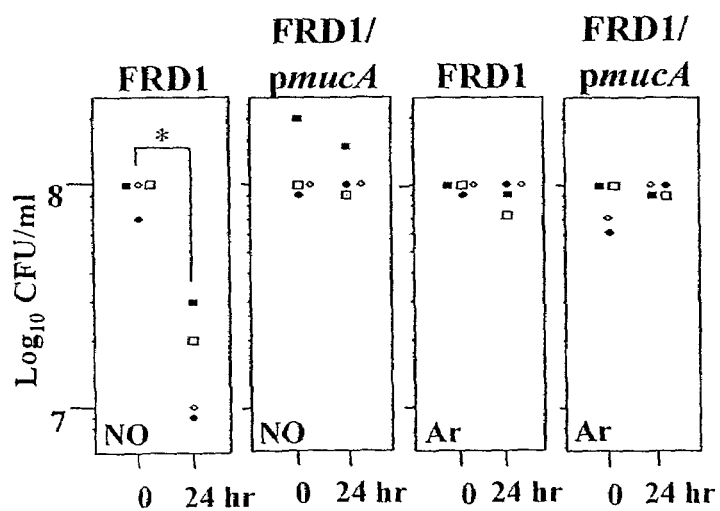
FIG. 10 shows the toxicity of NO gas, a by-product of acidified $NO_2^-$, towards FRD1 and FRD1/pmucA in LB at pH 6.5. A NO gas at 333 ppm is balanced with pure argon and continuously bubbled for 24 hr anaerobically.
Figure 11:
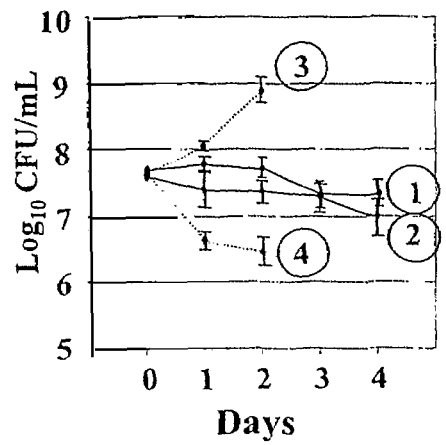
FIG. 11 shows that $ONOO^-$ is not formed in anaerobic PA cultures and that bacterial killing is not due to this species, because it cannot be produced in the absence of oxygen. PA PAO1 (line 1 and 3) and isogenic sodAsodB double mutants (lines 2 and 4) are grown in LB, pH 6.5 containing 15 mM $NO_2^-$ under aerobic (for 2 days, dotted lines) and anaerobic (for 4 days, solid lines) conditions. CFU are measured daily and plotted in logarithmic scale. For aerobic samples, strains are grown with vigorous shaking (300 rpm).

This analysis naturally supports the earlier statement that NO is responsible for the microbicidal action of acidified $NO_2^-$. It also allows the prediction that carboxy-PTIO should have a strong protective effect when added at millimolar concentrations. This effect is in fact shown in FIG. 9. In addition, the idea that NO is responsible for the microbicidal action of $NO_2^-$ is strongly supported by the observation that strain FRD1, but not FRD1/pmucA, is killed when an NO/Ar gas mixture is bubbled into a bacterial suspension; a 380 nM solution concentration of NO maintained in this experiment is comparable to that expected to be generated over 24 hr by 15 mM $NO_2^-$ (pH 6.5) (FIG. 10). In contrast, both strains maintain viability when treated with argon gas. In addition, FIG. 11 shows that an sodAsodB mutant of strain PAO1 is not sensitive to $HNO_2$ under aerobic conditions. This shows that $ONOO^-$ is not formed during anaerobic cultures and that bacterial killing is not due to this species.

Mucoid mucA mutant bacteria inherently harbor low anaerobic NOR and NIR activity. The molecular basis of NO sensitivity of mucoid mucA mutant bacteria is also of interest. The activity of enzymes involved in PA anaerobic respiration, including nitrate reductase (NAR), nitrite reductase (NIR) and nitric oxide reductase (NOR) has been studied. Mucoid FRD1 has ~3.7 fold higher NAR activity compared to nonmucoid FRD1/pmucA and PAO1. However, strain FRD1 possesses only ~4% and 20% the NIR and NOR activity, respectively, compared to strain PAO1. The reduced NOR activity in FRD1 explains, in part, the limited capacity for NO removal in this organism and its greater sensitivity to NO. The lack of NIR activity in strain FRD1 indicates the failure of $NO_2^-$ to support anaerobic growth of this strain. When $NO_2^-$ levels are measured in the FRD1 culture media after 4 days, there is little loss of $NO_2^-$, confirming the low levels of respiratory NIR activity. In addition, the low NIR activity in strain FRD1 leads to the constancy of the $HNO_2$ levels in the culture medium and the attendant increase in NO levels, compared to strains that metabolize $NO_2^-$. Interestingly, FRD1/pmucA possesses ~2-fold higher NO consumptive activity compared to strain PAO1, suggesting a positive correlation of NOR activity with the presence of multiple copies of wild-type MucA. Finally, because NOR activity is significantly reduced in mucoid bacteria, mucoid organisms completely devoid of NOR activity are more sensitive to acidified $NO_2^-$. The nor CB mutant of FRD1 is ~10-fold more sensitive than strain FRD1 to $NO_2^-$ (pH 6.5).

The detailed description will be more fully understood in view of the following more specific examples. The following examples are provided to illustrate the methods and various embodiments of the present invention. While the examples focus on the treatment of *Pseudomonas aeruginosa* as the bacterial respiratory tract infection, similar results can be obtained with other bacterial infections. The use of this treatment on other bacterial respiratory tract infections will be apparent to one of ordinary skill in the art and are within the scope of the claims.

EXAMPLES

Materials and Methods

Throughout the examples, the following experimental procedures may be referenced:

Bacterial Culture Conditions and Viable Cell Counting

The PA strains used in this study include laboratory strains PAO1 (5), CF isolate FRD1 (6), other sputum isolates from CF patients, and sixteen mucoid isolates. Complementation of the mucA mutant allele of strain FRD1 is achieved by transformation with ptacmucA. Aerobic starter cultures are grown in L-broth (10 g tryptone, 5 g NaCl and 5 g yeast extract, per liter) at 37° C. Anaerobic growth is achieved in an anaerobic chamber (Coy Laboratories, Grass Lake, Mich.) in an atmosphere of $N_2$ (85%), $CO_2$ (5%) and $H_2$ (10%). To support anaerobic respiration, $KNO_3$ and/or $NaNO_2$ are added to the medium. The pH of the medium is adjusted with 100 mM sodium phosphate (for pH 6.5) or 100 mM sodium acetate (for pH 5.5). To enumerate viable cells in cultures, colony forming units (CFU) are determined. Organisms are serially diluted in sterile 0.9% saline and 10 µl suspensions of $10^{-1}$ through $10^{-6}$ serial dilutions are spotted on L-agar plates and incubated at 37° C. under aerobic conditions for 15 hr.

$NO_2^-$ Sensitivity and Enzyme Activity Assays

Thirty µl of aerobic starter cultures of strain FRD1 or FRD1/pmucA are mixed with 3 ml of prewarmed sterile 0.7% low-melt agarose and spread on L-agar plates and a sterile filter disk impregnated with 10 µl of 1 M $NO_2^-$ is placed in the center of each plate. Plates are incubated for 2 days under anaerobic conditions. To support anaerobic growth, 15 mM $NO_3^-$ is included in the media.

NO Exposure Studies

Nitric oxide (NO) gas (200 ppm, 0.4 µM) balanced with Ar is anaerobically delivered to a water-jacketed chamber in which ~$10^8$ bacteria/ml are suspended. This level of NO is consistent with those generated by the chemical reduction of $NO_2^-$. Gas flow is constantly maintained at 3 ml/min. Pure Ar gas is used as a control.

Confocal Examination of Biofilms

An 8-chambered coverslip system (Lab-Tek Inc., Campbell, Calif.) is used for biofilm architecture and viability experiments. L-broth containing 1% $KNO_3$ (400 µl) is inoculated with 4 µl of aerobic starter culture of mucA mutant, FRD1. After a 24 hr anaerobic incubation at 37° C., the FRD1 biofilms are washed 3 times with sterile 0.9% saline. The 1-day old anaerobic FRD1 biofilms are treated with $NO_2^-$ at pH 6.5 and 7.5 for 2 days. Bacterial viability staining and image acquisition are accomplished as described previously by Sparkman et al.

Measurement of pH in Airway Secretions

"In situ" pH measurements of mucopurulent airway secretions from CF airways are made by inserting the tip of a pH microelectrode (MI-413, Microelectrodes Inc., Bedford, N.H.) into collected mucopurulent secretions from lobar, segmental and subsegmental bronchi of freshly explanted lungs from 9 CF patients. Doctors remove the lungs at the time of organ transplantation. Duplicate measurements are recorded at 3 different sites in lobar bronchi and in 5-6$^{th}$ generation airways and the mean value from each patient is used for analysis.

Preparation of Sterile Ultrasupernatants of CF Airway Secretions

Purulent secretions are harvested from the airways of CF lungs which physicians remove at the time of lung transplantation. Experimenters then centrifuge the purulent secretions (100,000×g for 1 hr) and pass them through a sterile filter (0.22 µm, Costar 8110 mStar® LB Corning, N.Y.).

Effects of $NO_2^-$ on Killing of FRD1 and FRD1/pmucA in Mouse Lung

CD1 mice are infected with ~$10^6$ FRD1 or FRD1/pmucA entrapped in agar beads intratracheally. Following 24 hr incubation, they intranasally administer 50 µl of 50 mM potassium phosphate (pH 6.5) containing 15 mM $NO_2$-3 times daily. On the fifth day, the mice are sacrificed and the viable bacteria from the lung homogenates are enumerated.

Biological Function Measurements of $NO_2^-$ Treated Airway Epithelial Cells

A primary culture of human airway epithelial cells is performed. Cellular cytotoxicity is assessed by comparing release of lactate dehydrogenase (LDH) into the basolateral media of cultured airway epithelial cell preparations treated apically with 2 µl of saline supplemented with $NO_2^-$. LDH is measured using a commercially available spectrophotometric assay kit (Biovision Research Products, Mountain View, Calif.) according to the manufacturer's instructions. Then, the bioelectric properties of cultured airway epithelial cells are analyzed.

For experiments measuring transepithelial water flux, the primary cultures of airway epithelia are cultured in a specially humidified incubator, to prevent evaporative water loss from the culture surface. The culture preparations are treated apically with 100 µl of Krebs bicarbonate Ringer's (KBR) solution containing 2% blue dextran (BD), (a cell-impermeable volume marker dye) supplemented with 15 mM $NO_2^-$. After 24 hr, microaliquots (2-5 µl) of apical liquid are collected and stored at -20° C. until analyzing. BD concentration is measured optically and IL-8 concentrations in basolateral media are measured using commercially available antibody pairs (R&D Systems, Minneapolis, Minn.) according to the manufacturer's instructions. The correlation coefficient for the assay is >0.996. To measure $NO_2^-$ half-life on the surface of cultured airway epithelia, triplicate preparations of cultured human airway epithelium from 4 CF patients are treated apically with 300 µl of KBR supplementing with varying concentrations of $NO_2^-$. At various time points, aliquots of apical liquid are aspirated and stored at -20° C. $NO_2^-$ levels are measured by the Griess reaction (42) and the percent rate of $NO_2^-$ removal is calculated.

All bacteria are derivatives of *P. aeruginosa* PAO1 (5). Allelic exchange are used for deletion or insertion mutagenesis. Bacteria are grown in either Luria-Bertani (L)-broth or L-broth containing 1% $KNO_3$ (LBN).

Example 1

This example shows $NO_2^-$ as an effective treatment for mucoid PA infections in in vitro anaerobic biofilms and fresh sputum isolates from CF patients.

Figure 12:
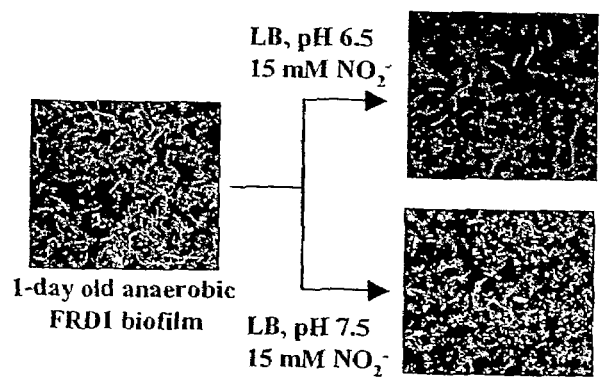
FIG. 12 shows the effect of $HNO_2$ on killing PA in biofilms and fresh sputum isolates. For the confocal laser microscopic analysis of anaerobic FRD1 biofilms, live cells are stained with syto-9, and dead cells are stained with propidium iodide. Top (x-y plane) views are projected from a stack of 125 images taken at 0.4 µm intervals for a total of 50 µm. Before staining, 1-day old anaerobic FRD1 biofilms are treated anaerobically with 15 mM $NO_2^-$ at pH 6.5 (top right) and 7.5 (bottom right) for 2 days. The top right box shows that the majority of bacteria are killed at a pH of 6.5, while the bottom right box shows that the majority of the bacteria remain viable at a pH of 7.5.
Figure 13:
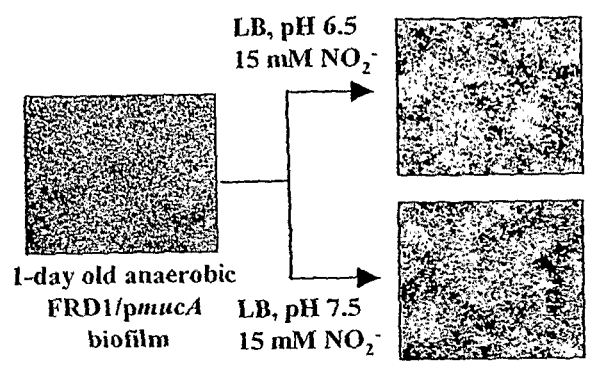
FIG. 13 shows the effect of $HNO_2$ on killing PA in biofilms and fresh sputum isolates, where the biofilms are grown using non-mucoid FRD1/pmucA. The non-mucoid FRD1/pmucA shows at least some resistance to acidified $NO_2^-$.

To explore the potential clinical application of $HNO_2$ in the treatment of mucoid PA infections in chronic CF patients, the effect of $NO_2^-$ on the viability of biofilm bacteria is tested. Anaerobic biofilms of strains FRD1 and FRD1/pmucA are grown for 1 day in media containing $NO_3^-$, which supports anaerobic respiration. Since mucoid strain FRD1 lacks a flagellum, a surface appendage that is critical for PA biofilm initiation, strain FRD1 forms much weaker biofilms compared to those of flagellated FRD1/pmucA (FIG. 12 vs. FIG. 13). When the FRD1 biofilm is treated with $NO_2^-$ at pH 7.5 for 2 days, no difference in biofilm structure and cell viability is observed relative to control biofilms. In contrast, nearly complete death of biofilm organisms is observed after a 2-day incubation with $NO_2^-$ at pH 6.5 (FIG. 12). In biofilms of FRD1/pmucA, however, resistance to acidified $NO_2^-$ is clearly evident (FIG. 13).

Figure 14:
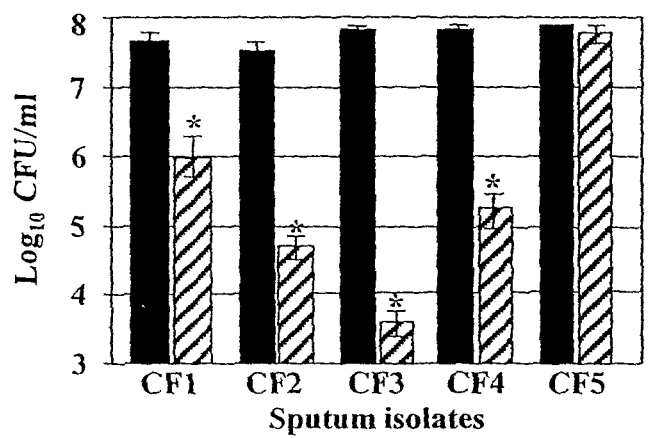
FIG. 14 shows the toxicity of 15 mM $NO_2^-$ (pH 6.5) towards PA sputum isolates. Viable cells in the initial inoculum (solid bars) and after a 24 hr anaerobic incubation (hatched bars) are presented in logarithmic scale. CF1-4 are mucoid mucA mutants and CF5 is nonmuoid and possesses a wild type mucA gene.

The effect of $HNO_2$ on the killing of sputum isolates from CF patients is also monitored. Sputum isolates CF-1, -2, -3 and -4 harbor nearly 100% mucoid mucA mutant bacteria while the CF-5 isolate harbor only nonmucoid MucA-proficient PA (FIG. 14). To minimize loss of the properties acquired in vivo, these isolates are passed only once in L-broth and immediately assayed for anaerobic $NO_2^-$ sensitivity. When these isolates are exposed to 15 mM $NO_2^-$ at pH 6.5 under anaerobic conditions for 1 day, a sharp decrease in viability is observed in the mucoid mucA mutant isolates. Again, the inherent utility of these isolates is that they are freshly isolated from CF patients and are not from long-term frozen stocks derived from CF patients. These results clearly indicate that high levels of $HNO_2$ selectively kill mucoid mucA mutant PA.

Example 2

This example shows $HNO_2$ kills mucoid PA in a sterile ultrasupernatant derived from explanted CF lungs and in mouse airways.

Figure 15:
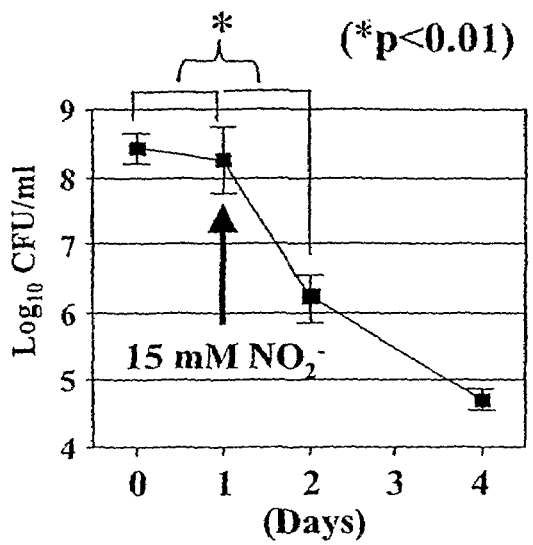
FIG. 15 shows the applications of $HNO_2$ mediated killing of mucoid PA to clinical specimens, including, the killing of FRD1 by $NO_2^-$ in sterile ultrasupernatants of CF airway secretions derived from explanted CF lungs. Bacteria are incubated anaerobically for 24 hr and 15 mM $NO_2^-$ is added (arrow). CFU are determined (n=3) and plotted as the X±SEM vs. time.

Next, it is determined whether mucoid strain FRD1 can be killed by $HNO_2$ in sterile ultrasupernatants (pH 6.24) of CF airway secretions derived from explanted CF lungs. This reagent arguably represents the best medium to investigate PA in the context of bacterial growth and the effects of $HNO_2$ ex vivo. FIG. 15 shows that mucoid bacteria are actually killed faster by $HNO_2$ in the CF ultrasupernatants than in L-broth (refer to FIG. 4).

Figure 16:
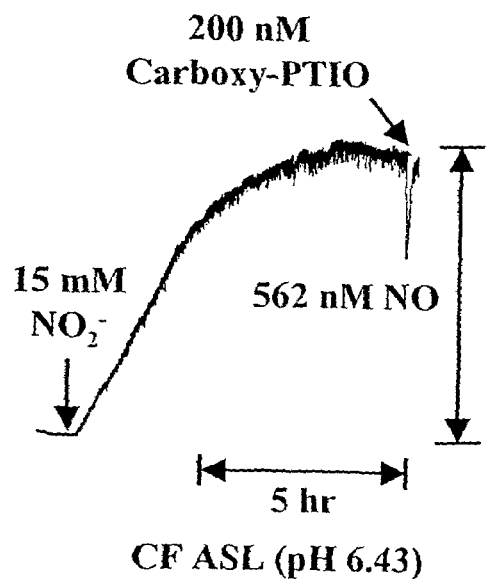
FIG. 16 shows the NO generation in CF ASL (airway surface liquid) by 15 mM $NO_2^-$.

Next, NO levels generated from $HNO_2$ disproportionation in ASL is collected from primary CF airway epithelia and measured. FIG. 16 indicates that NO, at levels even greater (562 nM) than those generated in LB at pH 6.5 (489 nM, refer to FIG. 8), is produced in CF ASL. The higher levels of NO produced upon addition of $NO_2^-$ in this milieu are due to the lower pH of the sample (6.43 vs. 6.5).

Figure 17:
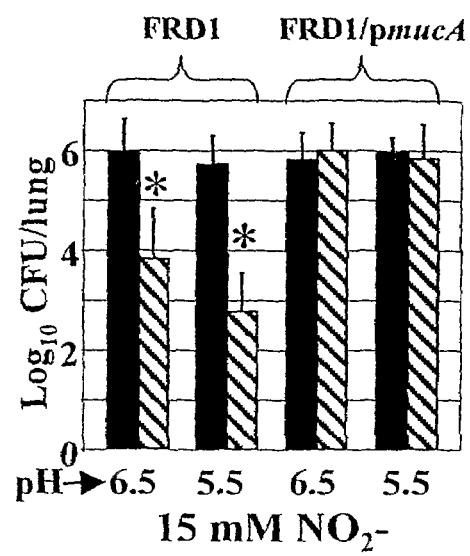
FIG. 17 shows the effects of $NO_2^-$ on killing of mucoid FRD1 and non-mucoid FRD1/pmucA in mouse lungs. CD1 mice are infected with FRD1 or FRD1/pmucA. Infected mice are treated with buffer (black bars) and buffered $NO_2^-$ (hatched bars) daily and viable bacteria from the lung homogenates are enumerated.

The efficacy of $HNO_2$ to kill strain FRD1 in a PA chronic lung infection model is then determined. Currently, there is no animal model for the anaerobic biofilm mode of CF airway disease or a CF animal that acquires spontaneous PA infections. However, CD1 mice, inoculated with agarose beads impregnated with bacteria, are useful for studying chronic lung infection by PA. Consistent with the in vitro results, mucoid FRD1, but not nonmucoid FRD1/pmucA, are decreased >2 logs at pH 6.5 and >3 logs at pH 5.5 by $HNO_2^-$ in vivo (FIG. 17). Because NO concentrations derive from acidified $NO_2^-$ are 10-fold greater with a reduction of 1 pH unit, the results are consistent with classical $NO_2^-$ reduction chemistry. Furthermore, organisms that are recovered from the mouse airways after $NO_2^-$ exposure are still sensitive to $NO_2^-$ in vitro.

Figure 18:
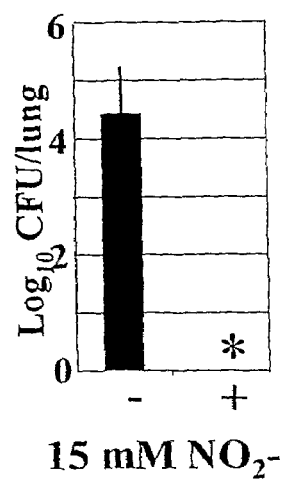
FIG. 18 shows the effects of long-term $NO_2^-$ treatment on the killing of FRD1 in mouse lungs. Another group of FRD1-infected mice are treated daily with buffer (50 mM sodium phosphate, pH 6.5) or buffer with 15 mM $NO_2^-$ for 16 days. Organisms surviving treatment with buffer (−) and $NO_2^-$(+).

To address whether long-term treatment with $HNO_2$ produced progressively decreasing airway titers of mucoid, mucA mutant bacteria, $NO_2^-$ is instilled on a daily basis in mice infected with mucoid organisms for a period of 16 days. FIG. 18 shows that there is no bacteria detected in mice treated for 16 days with $HNO_2$, while buffer control mice still harbor nearly $10^4$ mucoid organisms per lung.

Figure 19:
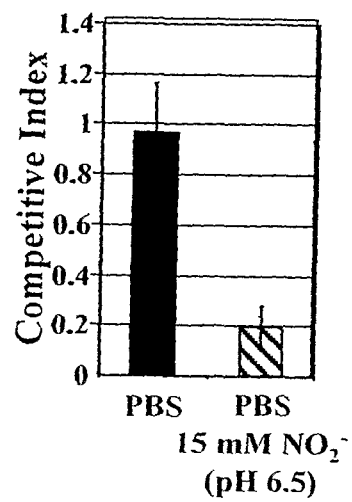
FIG. 19 shows competitive index experiments with $10^6$ FRD1 and FRD1/pmucA intratracheally instilled into CD1 mouse airways and incubated for 6 days prior to harvesting of mouse lungs and enumeration of CFU after homogenization. The black bars indicate PBS control mice while the hatched bars indicate $NO_2^-$ treated mice.

To address the possibility that acidified $HNO_2$ can kill mucoid mucA mutant bacteria in the presence of nonmucoid bacteria in vivo (similar to the results obtained in vitro in FIG. 1), competitive index experiments are performed. FIG. 19 demonstrates that the competitive index is only ~0.2 for mucoid, mucA mutant strain FRD1 relative to its complemented strain, FRD1/pmucA, which was ~1.0.

Example 3

This example shows that $NO_2^-$ does not elicit any adverse effects on airway epithelia in vitro.

Figure 20:
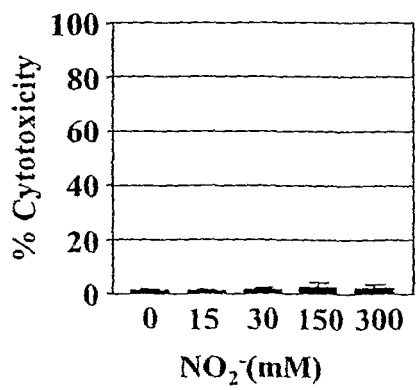
FIG. 20 shows that $NO_2^-$ has little or no effect on viability of cultured human airway epithelia. Culture preparations of human CF airway epithelium (duplicate preparations, n=3) are exposed apically to 2 µl of varying concentrations of $NO_2^-$. After 24 hr, LDH activity in the basolateral media is measured to monitor cytotoxicity.

The clinical utility of $NO_2^-$ as a treatment would be diminished if it exerted significant toxic or adverse effects on airway epithelia. Therefore, the effect of $NO_2^-$ on cell viability and function of cultured airway epithelia is tested. Further, since $NO_2^-$ could elicit a pro-inflammatory response that would be undesirable in the CF airways, and NO has been reported to increase IL-8 gene transcription in a lung epithelial cell line, whether $NO_2^-$ induces IL-8 release from cultured airway epithelia is also tested. Aerosolization, a potential therapeutic delivery route for $NO_2^-$ to the CF airways, would deliver it in small volumes on the epithelial surface. To mimic this situation in vitro, a low volume (2 µl) of test solution containing various concentrations of $NO_2^-$ is added to the apical surface of CF airway epithelia at pH 6.5. Exposure to concentrations as high as 20 times the dose required to kill mucoid mucA mutant PA exert no cytotoxicity toward CF airway epithelia after 24 hr, as determined by lactate dehydrogenase release (FIG. 20). Such experiments are performed because aerosol exposure of any effective agent, regardless of treatment, requires that significantly higher concentrations (~25-fold) of stock solution be used so that appropriate doses are administered efficiently to the areas of interest.

Figure 21:
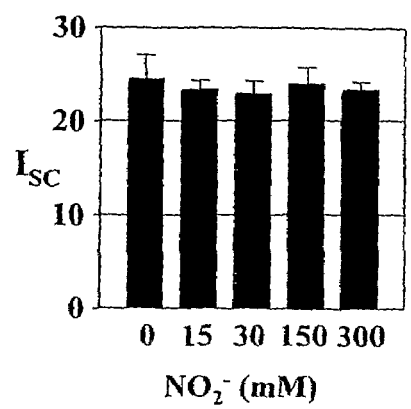
FIG. 21 shows that $NO_2^-$ does not affect the function of cultured airway epithelia as measured by transepithelial short circuit current. CF airway epithelial cultures are mounted in Ussing chambers and treated with 2 µl of liquid containing $NO_2^-$ at varying concentrations. Transepithelial short circuit current ($I_{sc}$ in $\mu A/Cm^2$) is measured to monitor any change in bioelectric properties.
Figure 22:
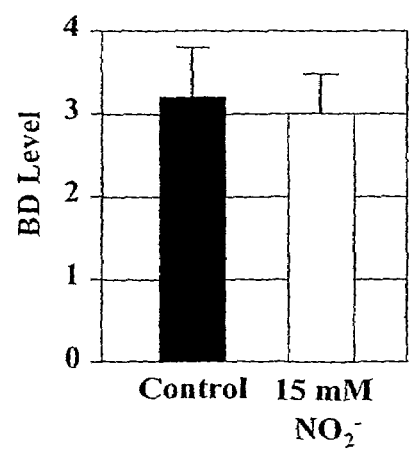
FIG. 22 shows $NO_2^-$ does not affect the function of cultured airway epithelia as measured by transepithelial water flux. CF airway epithelial cultures (triplicate preparations, n=4), are treated lumenally with 100 µl KBR buffer containing 2% blue dextran (BD) and supplemented with either 15 mM NaCl (black bar) or $NO_2^-$ (white bar) for 24 hr. Transepithelial water flux ($J_v$) is calculated by measuring BD concentration optically after 24 hr in microaliquots of sampled luminal liquid.
Figure 23:
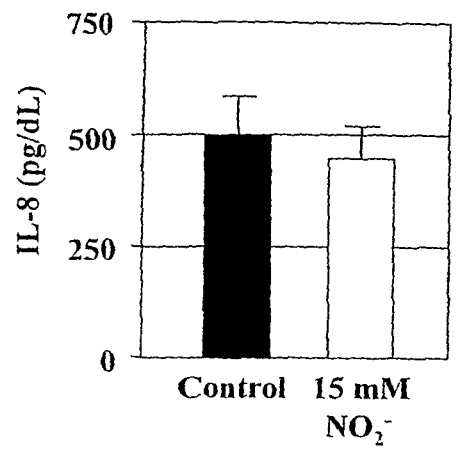
FIG. 23 shows $NO_2^-$ does not cause activation of an immune response as measured by release of the chemokine IL-8. The IL-8 release assay is performed using primary cultures of CF airway epithelia (n=4) which are exposed to 15 mM $NO_2^-$ (white bar) compared to control cultures (black bar).
Figure 24:
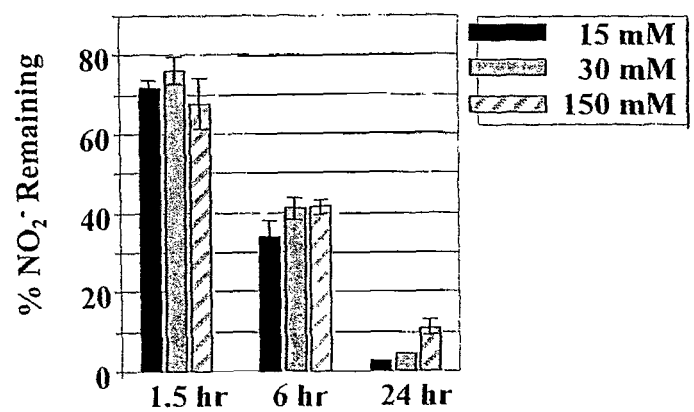
FIG. 24 shows the determination of $NO_2^-$ half-life on the surface of airway epithelia. The three different concentrations of $NO_2^-$ (15 mM, black bars; 30 mM, gray bars; 150 mM, hatched bars) are applied to airway epithelial cell monolayers and $NO_2^-$ levels are assayed at the given intervals (n=3 for each measurement).

In CF culture preparations mounted in Ussing chambers, basal transepithelial short circuit current ($I_{sc}$) is not affected by $NO_2^-$ exposure (FIG. 21). Further, 15 mM $NO_2^-$ fails to affect amiloride-sensitive $I_{sc}$ (control 15.4±1.4 vs. treated 15.7±1.7 µA/cm$^2$, p=0.92) and UTP-activated $I_{sc}$ (control 17.7±3.0 vs. treated 18.1±3.3 µA/cm$^2$, p=0.92). Consistent with these data, 15 mM $NO_2^-$ does not alter transepithelial water flux ($J_v$) in the same cultures (FIG. 22) or trigger IL-8 release over 24 hr in CF epithelia (FIG. 23). Finally, preliminary studies of the durability of $NO_2^-$ on CF airway surfaces are performed. The half-life of $NO_2^-$ is ~5 hr (FIG. 24), indicating that $NO_2^-$ is not immediately removed from the lumenal side of CF airway epithelia.

The specific embodiments and examples set forth above are provided for illustrative purposes only and are not intended to limit the scope of the following claims. Additional embodiments of the invention and advantages provided thereby will be apparent to one of ordinary skill in the art and are within the scope of the claims. All references cited within this disclosure are incorporated by reference herein.

1. Martin, D. W., Schurr, M. J., Mudd, M. H., and Deretic, V. 1993. Mechanism of conversion to mucoidy in *Pseudomonas aeruginosa* infecting cystic fibrosis patients. *Proc. Natl. Acad. Sci.* 90:8377-8381.
2. Anthony, M., Rose, B., Pegler, M. B., Elkins, M., Service, H., Thamotharampillai, K., Watson, J., Robinson, M., Bye, P., Merlino, J., et al. 2002. Genetic analysis of *Pseudomonas aeruginosa* isolates from the sputa of Australian adult cystic fibrosis patients. *J Clin Microbiol* 40:2772-2778.
3. Hassett, D. J. 1996. Anaerobic production of alginate by *Pseudomonas aeruginosa*: alginate restricts diffusion of oxygen. *J. Bacteriol.* 178:7322-7325.
4. Worlitzsch, D., Tarran, R., Ulrich, M., Schwab, U., Cekici, A., Meyer, K. C., Birrer, P., Bellon, G., Berger, J., Wei, T., et al. 2002. Reduced oxygen concentrations in airway mucus contribute to the early and late pathogenesis of *Pseudomonas aeruginosa* cystic fibrosis airway infection. *J. Clin. Invest.* 109:317-325.

5. Holloway, B. W. 1969. Genetics of *Pseudomonas*. *Bacteriol. Rev.* 33:419-443.
6. Goldberg, J. B., and Ohman, D. E. 1984. Cloning and expression in *Pseudomonas aeruginosa* of a gene involved in the production of alginate. *J. Bacteriol.* 158:1115-1121.

What is claimed is:

1. A method of treating an airway site of infection in a subject, comprising delivering a therapeutic amount of a nitrite composition to the airway site of infection via inhalation, wherein the airway site of infection comprises a mucoid *Pseudomonas aeruginosa* bacterial strain that contains a mutant mucA gene, wherein the airway site of infection has an acidic pH, wherein the inhalation is done using an inhaler, and wherein the device delivers 1-15 mM of nitrite.

2. The method according to claim 1, wherein the airway site of infection comprises mucus.

3. The method according to claim 1, wherein the airway site of infection comprises a bacterial biofilm.

4. The method according to claim 1, wherein the nitrite composition is acidified nitrite.

5. The method according to claim 1, wherein the therapeutic amount of nitrite composition is delivered to the airway site of infection via inhalation in a form selected from the group consisting of mist, aerosol, and dry powder.

6. The method according to claim 1, wherein the subject is diagnosed with a disease selected from the group consisting of cystic fibrosis, chronic obstructive pulmonary disease, black lung, pneumonia, and bronchiectasis.

7. A method of treating a respiratory tract bacterial infection at an airway site of infection in a subject, comprising delivering a therapeutic amount of a nitrite composition to the site of infection via inhalation and delivering a therapeutic amount of an antibiotic composition to the subject, wherein the infection comprises a bacterial strain that is a mucoid type *Pseudomonas aeruginosa*, wherein the airway site of infection has an acidic pH, wherein the inhalation is done using an inhaler, and wherein the device delivers 1-15 mM of nitrite.

8. A method of killing mucoid type *Pseudomonas aeruginosa* present in an airway site of infection of a subject diagnosed with cystic fibrosis, comprising delivering a therapeutic amount of nitrite composition to the airway via inhalation, wherein the mucoid type *Pseudomonas aeruginosa* present has low anaerobic nitric oxide reductase and nitrite reductase activity compared to nonmucoid *Pseudomonas aeruginosa*, wherein the airway site of infection has an acidic pH, and wherein the inhalation is done using an inhaler that delivers 1-15 mM nitrite.

9. The method of claim 1, wherein said nitrite composition is administered to deliver about 15 mM nitrite to airway surface liquid.

10. The method of claim 1, wherein said nitrite composition is administered to deliver about 1.5 mM nitrite to airway surface liquid.

11. The method of claim 1, wherein said nitrite composition is administered to deliver about 3 mM nitrite to airway surface liquid.

12. The method of claim 7, wherein said nitrite composition is administered to deliver about 15 mM nitrite to airway surface liquid.

13. The method of claim 7, wherein said nitrite composition is administered to deliver about 3 mM nitrite to airway surface liquid.

14. The method of claim 7, wherein said nitrite composition is administered to deliver about 1.5 mM nitrite to airways surface liquid.

15. The method according to claim 7, wherein the therapeutic amount of nitrite composition is delivered to the airway site of infection via inhalation in a form selected from the group consisting of mist, aerosol, and dry powder.

* * * * *